(12) United States Patent
Song et al.

(10) Patent No.: US 11,963,879 B2
(45) Date of Patent: Apr. 23, 2024

(54) FEMORAL PROSTHESIS AND KNEE PROSTHESIS WITH THEM

(71) Applicant: Beijing Naton Medical Technology Holdings Co., Ltd., Beijing (CN)

(72) Inventors: Dayong Song, Beijing (CN); Senyuan Hu, Beijing (CN); Xiang Dong, Beijing (CN)

(73) Assignee: BEIJING NATON MEDICAL TECHNOLOGY HOLDINGS CO., LTD., Beijing (CN)

( * ) Notice: Subject to any disclaimer, the term of this patent is extended or adjusted under 35 U.S.C. 154(b) by 28 days.

(21) Appl. No.: 17/561,690

(22) Filed: Dec. 23, 2021

(65) Prior Publication Data

US 2023/0058000 A1 Feb. 23, 2023

(30) Foreign Application Priority Data

Aug. 20, 2021 (CN) .......................... 202110961342.X

(51) Int. Cl.
*A61F 2/38* (2006.01)
*A61F 2/30* (2006.01)

(52) U.S. Cl.
CPC .......... *A61F 2/3836* (2013.01); *A61F 2/3859* (2013.01); *A61F 2002/30329* (2013.01)

(58) Field of Classification Search
CPC ................. A61F 2/3836; A61F 2/3859; A61F 2002/30329; A61F 2/389; A61F 2002/2825
See application file for complete search history.

(56) References Cited

U.S. PATENT DOCUMENTS 8,834,575 B2 *  9/2014  Wyss ................... A61F 2/3859
                                                    623/20.27
9,937,049 B2    4/2018  Wyss et al.
(Continued)

FOREIGN PATENT DOCUMENTS

CN       103796617 A        5/2014
CN       206120506          4/2017
(Continued)

OTHER PUBLICATIONS

DPM, Office Action for DE Application No. 10 2022 100 212.8, dated Mar. 23, 2023.
(Continued)

*Primary Examiner* — Matthew J Lawson
*Assistant Examiner* — Yasniary De La Caridad Morales
(74) *Attorney, Agent, or Firm* — Hodgson Russ LLP

(57) ABSTRACT

A femoral prosthesis includes a femur body and a cam portion. A joint surface of the femur body has a first joint surface portion for abutting a tibial prosthesis within a first knee flexion angle range from a first knee flexion angle to a second knee flexion angle, and a second joint surface portion for abutting the tibial prosthesis within a second knee flexion angle range from the second knee flexion angle to a third knee flexion angle. At the second knee flexion angle, the first joint surface portion has a first radius of curvature, and the second joint surface portion has a second radius of curvature. A center of a circle of an anterior joint surface of the cam portion is located in a first quadrant of a circle with the second radius of curvature in a sagittal section when the femoral prosthesis is in an extended state.

18 Claims, 3 Drawing Sheets

(56) References Cited

U.S. PATENT DOCUMENTS

| | | | |
|---|---|---|---|
| 2004/0162620 A1 | 8/2004 | Wyss | |
| 2012/0323334 A1* | 12/2012 | Jones | A61B 17/155 |
| | | | 623/20.14 |
| 2019/0328535 A1* | 10/2019 | Drury | A61F 2/3859 |
| 2020/0330236 A1* | 10/2020 | Hu | A61F 2/3859 |

FOREIGN PATENT DOCUMENTS

| | | |
|---|---|---|
| CN | 106821552 | 6/2017 |
| CN | 207755429 | 8/2018 |
| CN | 111821071 A | 10/2020 |
| CN | 113164260 | 7/2021 |
| EP | 3400912 | 11/2018 |
| JP | 2004321810 A | 11/2004 |
| WO | 9846171 A1 | 10/1998 |
| WO | 2012077755 A1 | 6/2012 |

OTHER PUBLICATIONS

CNIPA, First Office Action for CN Application No. 202110961342.X, dated May 20, 2023.

* cited by examiner

FEMORAL PROSTHESIS AND KNEE PROSTHESIS WITH THEM

CROSS-REFERENCE TO RELATED APPLICATIONS

This application claims priority to Chinese Patent Application Serial No. 202110961342.X, filed on Aug. 20, 2021, the entire disclosure of which is incorporated herein by reference.

FIELD

This application relates to the field of medical instruments and, more particularly, to a femoral prosthesis and a knee prosthesis having the same.

BACKGROUND

In knee arthroplasty, artificial knee prostheses are used to replace diseased articular cartilage and meniscus, while normal joint ligaments and other tissues are preserved, which may have the advantages of less trauma, faster recovery, reduced pain, and a more natural range of motion, so the knee arthroplasty is widely applied in knee treatment. However, the artificial knees in the related art are not reasonably designed, resulting in a high amount of intercondylar osteotomy of the knees, and raising a risk of knee fracture.

SUMMARY

A femoral prosthesis according to embodiments of the present disclosure is adapted to be mounted to a human femur and cooperate with a tibial prosthesis on a human tibia. The femoral prosthesis includes: a femur body having a joint surface, the joint surface of the femur body including: a first joint surface portion for abutting the tibial prosthesis within a first knee flexion angle range from a first knee flexion angle to a second knee flexion angle, the first knee flexion angle being 0° and smaller than the second knee flexion angle, and a second joint surface portion for abutting the tibial prosthesis within a second knee flexion angle range from the second knee flexion angle to a third knee flexion angle, the second knee flexion angle being smaller than the third knee flexion angle; and a cam portion coupled to the femur body. At the second knee flexion angle, the first joint surface portion has a first radius of curvature, and the second joint surface portion has a second radius of curvature. A joint surface of the cam portion initially contacting a protuberance of the tibial prosthesis is an anterior joint surface when the femoral prosthesis moves from an extended state to a flexed state, and a center of a circle of the anterior joint surface of the cam portion is located in a first quadrant of a circle with the second radius of curvature in a sagittal section when the femoral prosthesis is in the extended state.

A knee prosthesis, according to other embodiments of the present disclosure, includes: a tibial prosthesis including a tibial body and a protuberance arranged at an upper end of the tibial body; and a femoral prosthesis mounted to a human femur and cooperating with the tibial prosthesis. The femoral prosthesis includes: a femur body having a joint surface, the joint surface of the femur body including: a first joint surface portion for abutting the tibial prosthesis within a first knee flexion angle range from a first knee flexion angle to a second knee flexion angle, the first knee flexion angle being 0° and smaller than the second knee flexion angle, and a second joint surface portion for abutting the tibial prosthesis within a second knee flexion angle range from the second knee flexion angle to a third knee flexion angle, the second knee flexion angle being smaller than the third knee flexion angle; and a cam portion coupled to the femur body. At the second knee flexion angle, the first joint surface portion has a first radius of curvature, and the second joint surface portion has a second radius of curvature. A joint surface of the cam portion initially contacting a protuberance of the tibial prosthesis is an anterior joint surface when the femoral prosthesis moves from an extended state to a flexed state, and a center of a circle of the anterior joint surface of the cam portion is located in a first quadrant of a circle with the second radius of curvature in a sagittal section when the femoral prosthesis is in the extended state. The cam portion and the femur body define a sliding gap, and the protuberance is fit in the sliding gap. The femur body is movable between the extended state and the flexed state relative to the tibial body. During the motion of the femoral prosthesis from the extended state to the flexed state, the first joint surface portion and the second joint surface portion sequentially come into contact with the tibial body, and the cam portion contacts the protuberance.

REFERENCE NUMERALS

Figure 1:
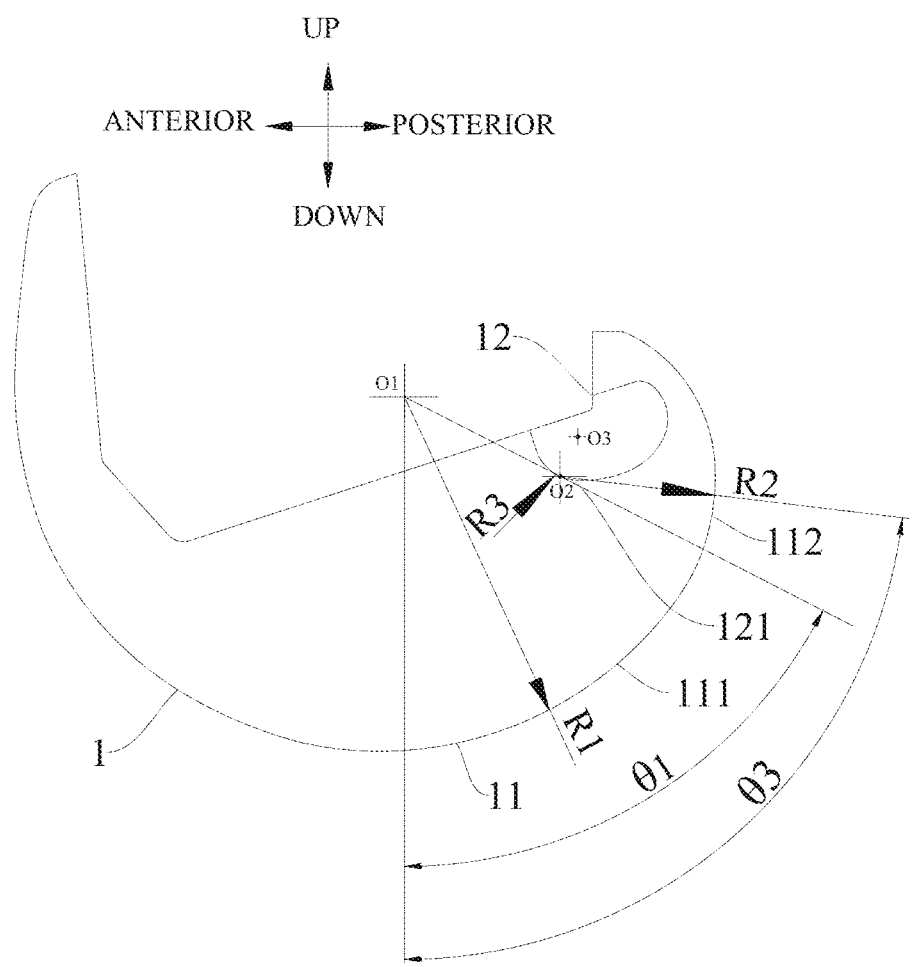
FIG. 1 is a schematic view of a femoral prosthesis according to an embodiment of the present disclosure.

1 femoral prosthesis; 11 femur body; 111 first joint surface portion; 112 second joint surface portion; 12 cam portion; 121 anterior joint surface; 13 sliding gap;

2 tibial prosthesis; 21 tibial body; 22 protuberance.

DETAILED DESCRIPTION OF EMBODIMENTS

Embodiments of the present disclosure will be described in detail below, and examples of the embodiments will be shown in the accompanying drawings. The embodiments described below are exemplary and are intended to explain the present disclosure rather than limit the present disclosure.

In order to better explain and understand the technical solutions of the present disclosure, directions and the like involved in the present disclosure will be clarified and illustrated in conjunction with the customary methods of description in the art.

In the field of anatomy and medical instruments, directions and surfaces such as "interior," "exterior," "anterior," "posterior," "distal," "proximal," "sagittal," "coronal," "cross-sectional," etc. have specific meanings and are well known to those skilled in the art, so these terms refer to the meanings recognized by those skilled in the art, unless otherwise specified.

Generally, three types of sections are usually involved in description on a human body, joint or prosthesis, namely, sagittal sections, coronal sections and cross sections. The sagittal section refers to a longitudinal section that divides the human body or joint into two parts (i.e., left and right parts) in a front-rear direction, and a sagittal section passing through the middle of the human body is a median sagittal section, which divides the human body into two equal parts. The coronal section refers to a longitudinal section that divides the human body or joint into two parts (i.e., front and rear parts) in a left-right direction, and the coronal section is perpendicular to the sagittal section. The cross section refers to a plane parallel to the ground plane and dividing the human body or joint into two parts (i.e., upper and lower parts), and the cross section is perpendicular to the coronal section and the sagittal section.

It can be understood that when the knee or knee prosthesis is described, the sagittal, coronal and cross sections refer to sections of a human standing normally upright, in which case a knee flexion angle is 0°. When the knee or knee prosthesis is extended and flexed, or when a posture of the human body is adjusted, the cross section may be changed accordingly.

Typically, three different types of orientations are involved in description on the human body, joint or prosthesis: distal and proximal, interior and exterior, and anterior and posterior. A distal end refers to an end of the human body or joint that is relatively far from the torso, and a proximal end refers to an end of the human body or joint that is relatively close to the torso. An interior side refers to a side relatively close to the median sagittal section of the human body, and an exterior side refers to a side relatively far from the median sagittal section of the human body. An anterior side refers to a side of the sagittal section that is relatively close to the abdomen, and a posterior side refers to a side of the sagittal section that is relatively close to the dorsum.

A femoral prosthesis and a knee prosthesis having the same according to embodiments of the present disclosure will be described below with reference to the accompanying drawings.

As shown in FIGS. 1-5, the femoral prosthesis 1 according to embodiments of the present disclosure is adapted to be mounted to a human femur and cooperates with a tibial prosthesis 2 on a human tibia. The femoral prosthesis 1 includes a femur body 11 and a cam portion 12 coupled to the femur body 11.

A joint surface of the femur body 11 has a first joint surface portion 111 for abutting the tibial prosthesis 2 within a first knee flexion angle range, and a second joint surface portion 112 for abutting the tibial prosthesis 2 within a second knee flexion angle range. The first knee flexion angle range is from a first knee flexion angle to a second knee flexion angle θ1, and the second knee flexion angle range is from the second knee flexion angle to a third knee flexion angle θ3.

The first knee flexion angle is 0°, and the first knee flexion angle is smaller than the second knee flexion angle that is in turn smaller than the third knee flexion angle. At the second knee flexion angle, a radius of curvature of the first joint surface portion 111 is a first radius of curvature R1, and a radius of curvature of the second joint surface portion 112 is a second radius of curvature R2.

In an extended state, a line of force of the human femur substantially coincides with a line of force of the human tibia. When the femoral prosthesis 1 moves from the extended state to a flexed state, a joint surface of the cam portion 12 initially contacting a protuberance 22 of the tibial prosthesis 2 is an anterior joint surface 121. In a sagittal section, a center O3 of a circle of the anterior joint surface 121 of the cam portion 12 is located in a first quadrant of a circle with the second radius of curvature when the femoral prosthesis 1 is in the extended state, a center of the circle with the second radius of curvature being denoted as O2.

Figure 2:
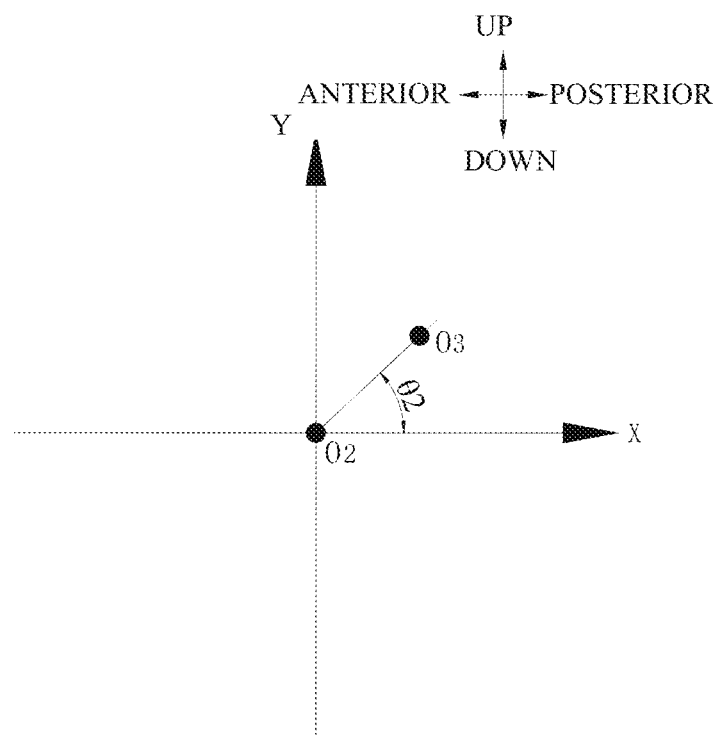
FIG. 2 illustrates a position of a center of a circle with a second radius of curvature of a femoral prosthesis in relation to a center of a circle of an anterior joint of a cam portion according to an embodiment of the present disclosure.
Figure 4:
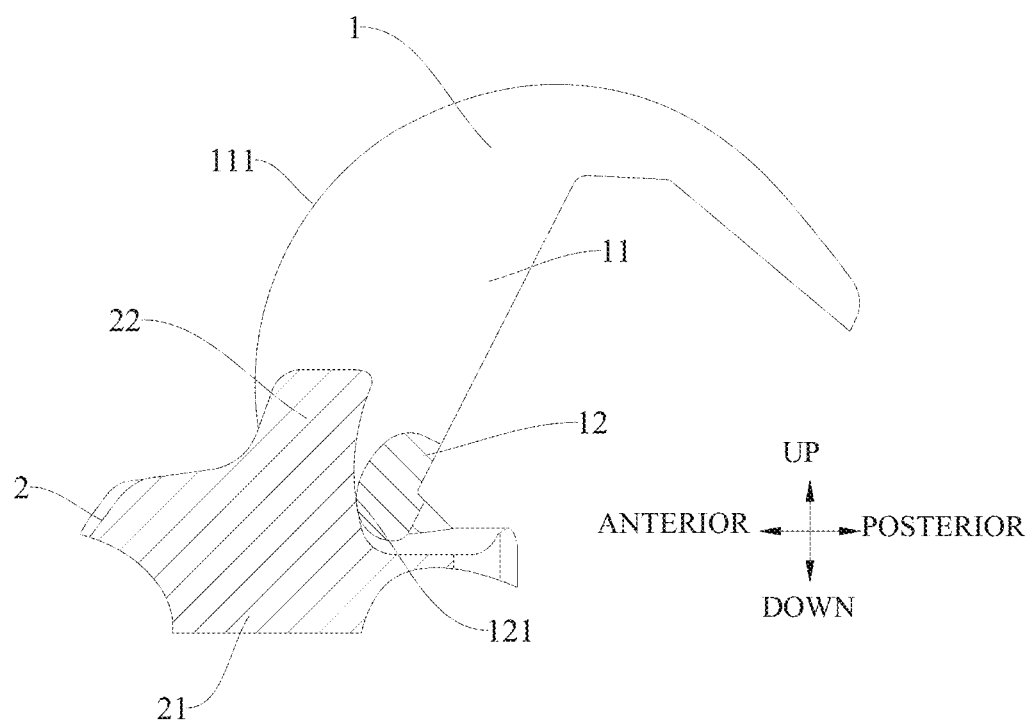
FIG. 4 is a sectional view of a knee prosthesis according to an embodiment of the present disclosure.
Figure 5:
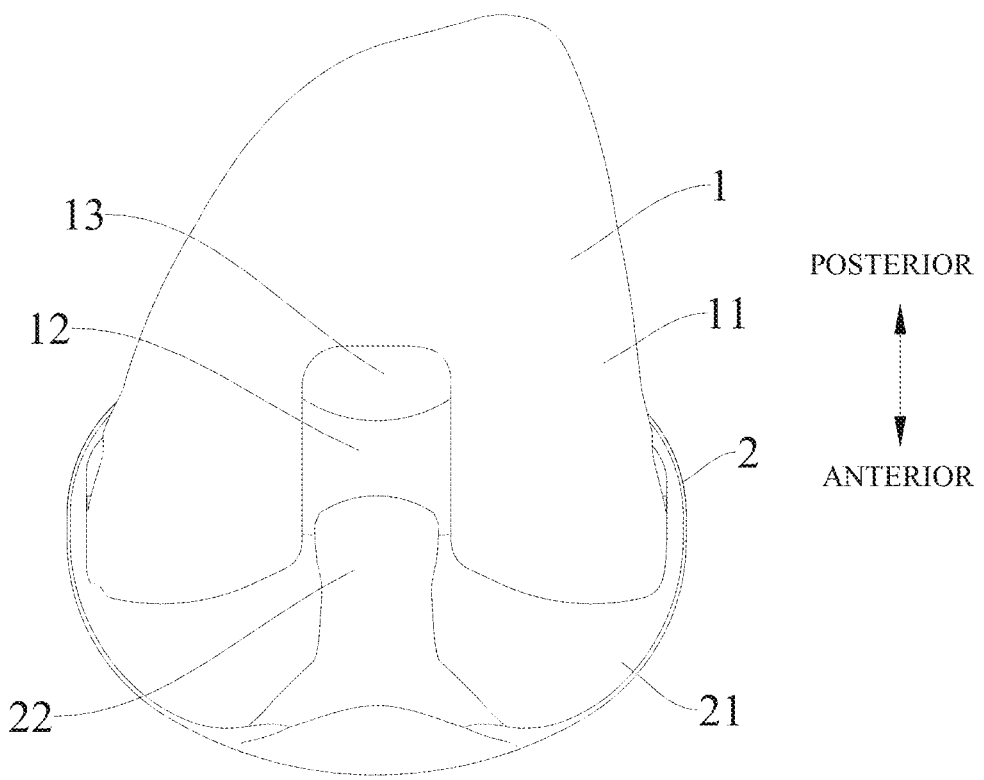
FIG. 5 is a side view of a knee prosthesis according to an embodiment of the present disclosure.

It can be understood that a rectangular coordinate system is established in the sagittal section with the center O2 of the circle of the second radius of curvature of the second joint surface portion 112 as an origin, as shown in FIGS. 1 and 2. An anterior-posterior direction of a tibial body 21 is an X-axis, and a direction from an anterior part to a posterior part of the tibial body 21 is a positive direction of the X-axis. The line of force of the human femur (an up-down direction of the femoral prosthesis 1 in FIG. 1) is a Y-axis, and a direction from a bottom part to a top part of the femoral prosthesis 1 is a positive direction of the Y-axis. As shown in FIGS. 4 and 5, an anterior side of the knee prosthesis is a side relatively close to the abdomen in the sagittal section of the human body, and a posterior side of the knee prosthesis is a side relatively close to the dorsum in the sagittal section of the human body.

As shown in FIGS. 1 and 2, when the femoral prosthesis 1 is in the extended state (the line of force of the human tibia substantially coincides with the line of force of the human femur), the center O3 of the circle of the anterior joint surface 121 is located in the first quadrant. In other words, the center O3 of the circle of the anterior joint surface 121 of the cam portion 12 is located behind and above the center O2 of the circle with the second radius of curvature of the second joint surface portion 112.

For the femoral prosthesis 1 according to the embodiments of the present disclosure, when the femoral prosthesis 1 is in the extended state, the center O3 of the circle of the anterior joint surface 121 of the cam portion 12 is located in the first quadrant of the circle with the center O2 and with the second radius of curvature in the sagittal section, allowing the cam portion 12 to be located closer to a posterior condyle of the knee, which in turn decreases the amount of intercondylar osteotomy of the knee, effectively reducing the risk of knee fracture. In addition, when the femoral prosthesis 1 according to the embodiments of the present disclosure moves from the extended state to the flexed state, the protuberance 22 can be limited by the cam portion 12, suppressing the abnormal forward motion of the femoral prosthesis 1, and improving the reliability of the knee prosthesis during use.

Due to the anatomical characteristics of the knee, the intercondylar bone mass on an anterior side of the knee is much larger than that on a posterior side of the knee, and the amount of intercondylar osteotomy of the knee depends on a position of the protuberance 22, in which the closer the protuberance 22 is to the anterior side, the larger the amount of intercondylar osteotomy of the knee, and when the protuberance 22 is close to the posterior side, the amount of intercondylar osteotomy of the knee is decreased. The position of the protuberance 22 is related to a position of the cam portion 12 on the femoral prosthesis 1, and the cam portion 12 moves in cooperation with the protuberance 22. A purpose of limiting the position of the protuberance 22 can be achieved by limiting the position of the cam portion 12.

For the femoral prosthesis 1 according to the embodiments of the present disclosure, the arrangement in the sagittal section where the center O3 of the circle of the anterior joint surface 121 of the cam portion 12 is located in the first quadrant of the circle with the center O2 and with the second radius of curvature allows the cam portion 12 to effectively approach a posterior condylar position of the femur body 11, and thus the protuberance 22 that cooperates with the cam portion 12 can also be designed to be close to the posterior side, effectively decreasing the amount of osteotomy in the posterior condylar position of the knee and reducing the risk of intercondylar fracture of the knee.

Figure 3:
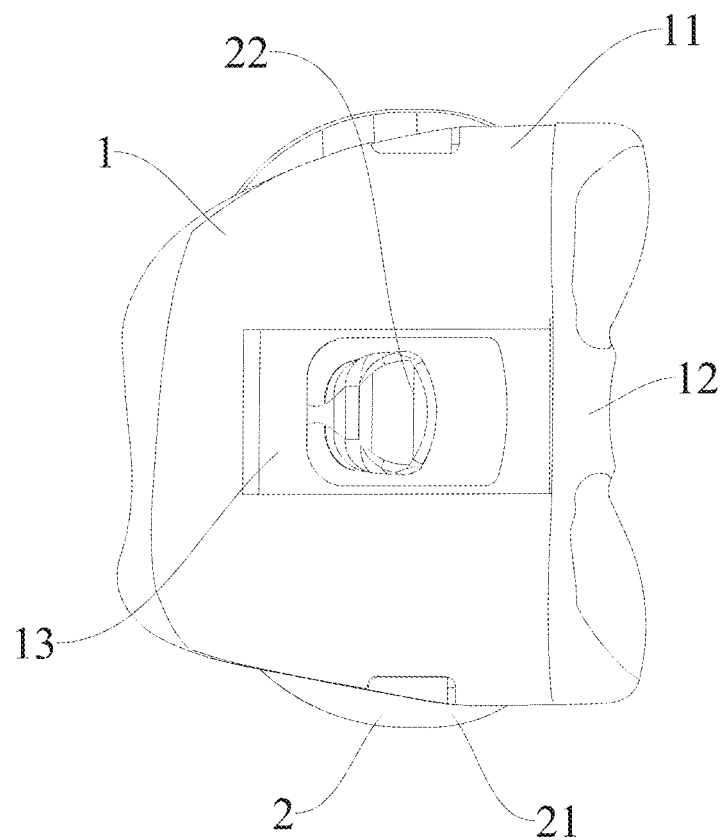
FIG. 3 is a top view of a knee prosthesis according to an embodiment of the present disclosure.

As shown in FIGS. 3-5, the tibial prosthesis 2 includes the tibial body 21 and the protuberance 22 located at an upper end of the tibial body 21. The cam portion 12 is coupled to the femur body 11 to define a sliding gap 13, and the protuberance 22 is fit in the sliding gap 13. The femur body 11 is coupled to the tibial body 21 and is rotatable between the extended state and the flexed state relative to the tibial body 21. During the motion of the femoral prosthesis 1 from the extended state to the flexed state (as shown in FIG. 4 where the femoral prosthesis 1 rotates clockwise relative to the tibial prosthesis 2), the first joint surface portion 111 and the second joint surface portion 112 sequentially come into contact with the tibial body 21 and the anterior joint surface 121 contacts the protuberance 22.

Further, as shown in FIG. 1 and FIG. 2, in the sagittal section, when the femoral prosthesis 1 is in the extended state, an angle between a line connecting the center O2 of the circle with the second radius of curvature and the center O3 of the circle of the anterior joint surface 121, and the anterior-posterior direction of the femur body 11 is $\theta 2$, where $0° \leq \theta 2 \leq 70°$. It can be understood that within the coordinate system established with the center O2 of the circle of the second radius of curvature of the second joint surface portion 112 as the origin, the anterior-posterior direction of the femur body 11 is the X-axis and the line of force of the human femur is the Y-axis. The angle $\theta 2$ between the line connecting the center O2 of the circle with the second radius of curvature and the center O3 of the circle of the anterior joint surface 121, and a positive half-axis of the X-axis satisfies $0° \leq \theta 2 \leq 70°$.

The inventors of the present application have found through experimental research that when the angle between the line connecting the center O2 of the circle with the second radius of curvature and the center O3 of the circle of the anterior joint surface 121, and the anterior-posterior direction of the femur body 11 satisfies the above range, the cam portion 12 can further effectively approach the posterior condylar position of the knee, further reducing the amount of osteotomy and reducing the probability of intercondylar fracture of the knee significantly.

In some embodiments, when the femoral prosthesis 1 moves from the extended state to the flexed state, the cam portion 12 comes into contact with the protuberance 22 of the tibial prosthesis 2 at the second knee flexion angle. It can be understood that during a knee flexion process, when the femoral prosthesis 1 moves from the first knee flexion angle range to the second knee flexion angle range, the first joint surface portion 111 of the femur body 11 first contacts the tibial prosthesis 2, and then the second joint surface portion 112 contacts the tibial prosthesis 2 as the knee flexion angle increases. When the first joint surface portion 111 of the femur body 11 is just about to separate from the tibial body 21 and the second joint surface portion 112 of the femur body 11 is just about to contact the tibial body 21, i.e., at the second knee flexion angle, the anterior joint surface 121 of a peripheral surface of the cam portion 12 contacts the protuberance 22 at the same time, allowing effective contact between the protuberance 22 and the cam portion 12 during the motion of the femoral prosthesis 1, inhibiting the abnormal forward motion of the femoral prosthesis 1, and improving the reliability of the femoral prosthesis 1 during its use.

Further, as shown in FIG. 1, in the sagittal section, a line connecting a center O1 of a circle with the first radius of curvature and the center O2 of the circle with the second radius of curvature is tangent to the anterior joint surface 121 of the cam portion 12 at the second knee flexion angle, to further inhibit the abnormal forward motion of the femoral prosthesis 1, make the structure of the femoral prosthesis 1 more reasonable and improve the use of the knee prosthesis.

Optionally, as shown in FIG. 1, the second knee flexion angle $\theta 1$ satisfies: $50° \leq \theta 1 \leq 70°$, and $\theta 1$ may be any angle in the range of 50° to 70°. For example, the center angle $\theta 1$ is 50°, 60°, 65° or 70°. The inventors of the present application have found through experimental research that when the second knee flexion angle $\theta 1$ is in the above range, the amount of wear of the knee prosthesis during motion can be further reduced, and a contact area between a femur joint surface and a tibia joint surface can keep consistent in a gait motion range of the human body, to maintain a maximum contact area of the knee prosthesis, decrease contact stress of the knee prosthesis, effectively reduce the wear of the knee prosthesis, and prolong the service life of the knee prosthesis.

Optionally, the third knee flexion angle $\theta 3$ satisfies $\theta 1 \leq \theta 3 \leq 90°$. The inventors of the present application have found through experimental research that when the third knee flexion angle $\theta 3$ is in the above range, the contact stress of the knee prosthesis can be reduced, effectively reducing the wear of the knee prosthesis and prolonging the service life of the knee prosthesis.

Further, as shown in FIG. 1, the first joint surface portion 111 has a first radius of curvature of R1 and the anterior joint surface 121 of the cam portion 12 has a radius of curvature of R3, wherein $0.05 \leq R3/R1 \leq 0.25$. Optionally, the value of R3/R1 is 0.05, 0.055, 0.01, 0.02, or 0.025. The inventors of the present application have found through experimental research that when the value of R3/R1 is smaller than 0.05, the cam portion 12 has a too small size, and a maximum flexion angle of the knee prosthesis cannot be achieved when the cam portion 12 is in contact with the protuberance 22; when the value of R3/R1 is greater than 0.25, the cam portion 12 has a too large size, and the cam portion 12 protrudes beyond the posterior condyle of the femur body 11, which also prevents the knee prosthesis from reaching the maximum flexion angle. Therefore, the inventors of the present application conclude that when $0.05 \leq R3/R1 \leq 0.25$, the structural dimension of the femoral prosthesis 1 can be optimized, resulting in a more reasonable design, longer service life and higher reliability of the femoral prosthesis 1.

In some embodiments, as shown in FIG. 1, a sagittal section of the first joint surface portion 111 may have a single first radius of curvature, which can ensure that the knee has a large contact area during the gait motion and a contact area between the femoral prosthesis 1 and the tibial prosthesis 2 keeps unchanged during the overall gait motion, effectively reducing the amount of wear of the knee prosthesis during the motion.

Optionally, a sagittal section of the second joint surface portion 112 has a radius of curvature that gradually decreases from an anterior end to a posterior end, allowing the second joint surface portion 112 and the tibial prosthesis 2 to maintain a maximum contact area of the knee prosthesis, decreasing the contact stress of the knee prosthesis, effectively reducing the wear of the knee prosthesis, and prolonging the service life of the knee prosthesis.

By way of example, in an embodiment of the present disclosure, the first knee flexion angle is 0°, the second knee flexion angle is 70°, and the third knee flexion angle is 90°.

In this embodiment, the sagittal section of the first joint surface portion 111 of the femur body 1 abutting the tibial prosthesis 2 has a single radius of curvature within the first knee flexion angle range of 0° to 70°, and the sagittal section of the second joint surface portion 112 of the femur body 1 abutting the tibial prosthesis 2 has a radius of curvature gradually decreasing from the anterior end to the posterior end within the second knee flexion angle range of 70° to 90°. For example, the second joint surface portion 112 has five different radii of curvature in the sagittal section, and values of the five different radii of curvature gradually decrease from the anterior end to the posterior end. Moreover, at the first knee flexion angle of 0°, the femoral prosthesis 1 is in the extended state, and the center O3 of the circle of the anterior joint surface 121 of the cam portion 12 is located in the first quadrant of the circle with the center O2 and with the second radius of curvature. Along with the knee flexion motion, at a knee flexion angle of 70°, the anterior joint surface 121 of the cam portion 12 comes into contact with the protuberance 22 of the tibial prosthesis 2. Thus, the amount of posterior condylar osteotomy of the knee can be reduced and the risk of intercondylar fracture of the knee can be lowered, while the wear of the knee prosthesis is effectively decreased and the service life of the knee prosthesis is prolonged.

It can be understood that in different embodiments of the present disclosure, the second knee flexion angle θ1 and the third knee flexion angle θ3 may be combined as long as they satisfy any value within the protection scope of the present disclosure, and the above-mentioned optional features can also be combined to constitute different embodiments, all of which fall into the protection scope of the present disclosure.

As shown in FIGS. 2-5, a knee prosthesis, according to other embodiments of the present disclosure, includes a femoral prosthesis 1 and a tibial prosthesis 2, the femoral prosthesis 1 being the femoral prosthesis 1 according to the above embodiments of the present disclosure. The tibial prosthesis 2 includes a tibial body 21 and a protuberance 22 arranged at an upper end of the tibial body 21. The cam portion 12 and the femur body 11 define a sliding gap 13, and the protuberance 22 is fit in the sliding gap 13. The femur body 11 is coupled to the tibial body 21 and is rotatable between the extended state and the flexed state relative to the tibial body 21. During the motion of the femoral prosthesis 1 from the extended state to the flexed state, the first joint surface portion 111 and the second joint surface portion 112 sequentially come into contact with the tibial body 21, and the cam portion 12 contacts the protuberance 22.

For the knee prosthesis according to the embodiment of the present disclosure, since the center O3 of the circle of the anterior joint surface 121 of the cam portion 12 is located in the first quadrant of the circle with the center O2 and with the second radius of curvature when the femoral prosthesis 1 is in the extended state, the cam portion 12 may be located closer to the posterior condylar position of the femur body 11, and the amount of intercondylar osteotomy of the knee can be reduced, effectively lowering the risk of knee fracture. In addition, as the knee prosthesis according to the embodiment of the present disclosure moves from the extended state to the flexed state, the protuberance 22 can be limited by the cam portion 12, and thus the abnormal forward motion of the femoral prosthesis 1 can be suppressed, improving the reliability of the knee prosthesis during its use.

In addition, terms such as "first" and "second" are used herein for purposes of description and are not intended to indicate or imply relative importance or significance or to imply the number of indicated technical features. Thus, the feature defined with "first" and "second" may include one or more of this feature. Reference throughout this specification to "an embodiment," "some embodiments," "an example," "a specific example," or "some examples," means that a particular feature, structure, material, or characteristic described in connection with the embodiment or example is included in at least one embodiment or example of the present disclosure. Thus, the appearances of these phrases in various places throughout this specification are not necessarily referring to the same embodiment or example of the present disclosure. Furthermore, the particular features, structures, materials, or characteristics may be combined in any suitable manner in one or more embodiments or examples. Moreover, different embodiments or examples as well as features in different embodiments or examples described in this specification may be integrated and combined.

It should be understood that the application of the present disclosure is not limited to the detailed construction and arrangement of components presented in this specification. The present disclosure may include other embodiments and may be implemented and performed in various ways. The foregoing variations and modifications fall within the scope of the present disclosure. It should be understood that the present application as disclosed and limited by this specification extends to all alternative combinations of two or more individual features mentioned or illustrated in the text and/or the drawings. All such different combinations constitute multiple alternative aspects of the present disclosure. Embodiments of the present disclosure elaborate the best implementation known for realizing the present disclosure and enable those skilled in the art to make use of the present disclosure.

What is claimed is:

1. A femoral prosthesis, configured to be mounted to a human femur and cooperating with a tibial prosthesis configured to be mounted on a human tibia, the femoral prosthesis comprising:
 a femur body having a joint surface, the joint surface of the femur body comprising:
   a first joint surface portion for abutting the tibial prosthesis within a first knee flexion angle range from a first knee flexion angle to a second knee flexion angle, the first knee flexion angle being 0° and smaller than the second knee flexion angle, and
   a second joint surface portion for abutting the tibial prosthesis within a second knee flexion angle range from the second knee flexion angle to a third knee flexion angle, the second knee flexion angle being smaller than the third knee flexion angle; and
 a cam portion coupled to the femur body,
 wherein:
   at the second knee flexion angle, the first joint surface portion has a first radius of curvature, and the second joint surface portion has a second radius of curvature;
   a joint surface of the cam portion configured to initially contact a protuberance of the tibial prosthesis is an anterior joint surface when the femoral prosthesis moves from an extended state to a flexed state, and a center of a circle of the anterior joint surface of the cam portion is located in a first quadrant of a rectangular coordinate system established with a center of a circle with the second radius of curvature in a sagittal section as an origin when the femoral prosthesis is in the extended state; and a line connecting a center of a circle with the first radius of curvature and a center of the circle with the second radius of curvature is tangent to the anterior joint surface of the cam portion at the second knee flexion angle in the sagittal section.

2. The femoral prosthesis according to claim 1, wherein an angle $\theta 2$ between a line connecting the center of the circle with the second radius of curvature and the center of the circle of the anterior joint surface and an anterior-posterior direction of the femur body in the sagittal section satisfies $0° \leq \theta 2 \leq 70°$, when the femoral prosthesis is in the extended state.

3. The femoral prosthesis according to claim 1, wherein the cam portion comes into contact with the protuberance of the tibial prosthesis at the second knee flexion angle when the femoral prosthesis moves from the extended state to the flexed state.

4. The femoral prosthesis according to claim 1, wherein the second knee flexion angle $\theta 1$ satisfies: $50° \leq \theta 1 \leq 70°$.

5. The femoral prosthesis according to claim 1, wherein the third knee flexion angle $\theta 3$ satisfies $\theta 3 \leq 90°$.

6. The femoral prosthesis according to claim 1, wherein the first radius R1 of curvature of the first joint surface portion and a radius R3 of curvature of the anterior joint surface of the cam portion satisfy $0.05 \leq R3/R1 \leq 0.25$.

7. The femoral prosthesis according to claim 1, wherein a sagittal section of the first joint surface portion has a single first radius of curvature.

8. The femoral prosthesis according to claim 1, wherein a sagittal section of the second joint surface portion has a radius of curvature gradually decreasing from an anterior end to a posterior end.

9. A knee prosthesis, comprising:
a tibial prosthesis comprising a tibial body and a protuberance arranged at an upper end of the tibial body; and
a femoral prosthesis configured to be mounted to a human femur and cooperating with the tibial prosthesis, the femoral prosthesis comprising:
a femur body having a joint surface, the joint surface of the femur body comprising:
a first joint surface portion for abutting the tibial prosthesis within a first knee flexion angle range from a first knee flexion angle to a second knee flexion angle, the first knee flexion angle being 0° and smaller than the second knee flexion angle, and
a second joint surface portion for abutting the tibial prosthesis within a second knee flexion angle range from the second knee flexion angle to a third knee flexion angle, the second knee flexion angle being smaller than the third knee flexion angle; and
a cam portion coupled to the femur body,
wherein:
at the second knee flexion angle, the first joint surface portion has a first radius of curvature, and the second joint surface portion has a second radius of curvature;

a joint surface of the cam portion initially contacting a protuberance of the tibial prosthesis is an anterior joint surface when the femoral prosthesis moves from an extended state to a flexed state, and a center of a circle of the anterior joint surface of the cam portion is located in a first quadrant of a rectangular coordinate system established with a center of a circle with the second radius of curvature in a sagittal section as an origin when the femoral prosthesis is in the extended state;

a line connecting a center of a circle with the first radius of curvature and a center of the circle with the second radius of curvature is tangent to the anterior joint surface of the cam portion at the second knee flexion angle in the sagittal section;

the cam portion and the femur body define a sliding gap, and the protuberance is fit in the sliding gap;

the femur body is movable between the extended state and the flexed state relative to the tibial body; and during motion of the femoral prosthesis from the extended state to the flexed state, the first joint surface portion and the second joint surface portion sequentially come into contact with the tibial body, and the cam portion contacts the protuberance.

10. The knee prosthesis according to claim 9, wherein an angle $\theta 2$ between a line connecting the center of the circle with the second radius of curvature and the center of the circle of the anterior joint surface and an anterior-posterior direction of the femur body in the sagittal section satisfies $0° \leq \theta 2 \leq 70°$, when the femoral prosthesis is in the extended state.

11. The knee prosthesis according to claim 9, wherein the cam portion comes into contact with the protuberance of the tibial prosthesis at the second knee flexion angle when the femoral prosthesis moves from the extended state to the flexed state.

12. The knee prosthesis according to claim 9, wherein the second knee flexion angle $\theta 1$ satisfies: $50° \leq \theta 1 \leq 70°$.

13. The knee prosthesis according to claim 9, wherein the third knee flexion angle $\theta 3$ satisfies $\theta 3 \leq 90°$.

14. The knee prosthesis according to claim 9, wherein the first radius R1 of curvature of the first joint surface portion and a radius R3 of curvature of the anterior joint surface of the cam portion satisfy $0.05 \leq R3/R1 \leq 0.25$.

15. The knee prosthesis according to claim 9, wherein a sagittal section of the first joint surface portion has a single first radius of curvature.

16. The knee prosthesis according to claim 15, wherein a contact area between the femoral prosthesis and the tibial prosthesis keeps unchanged during motion.

17. The knee prosthesis according to claim 9, wherein a sagittal section of the second joint surface portion has a radius of curvature gradually decreasing from an anterior end to a posterior end.

18. The knee prosthesis according to claim 17, wherein the second joint surface portion and the tibial prosthesis maintain a maximum contact area of the knee prosthesis.

* * * * *